(12) United States Patent
Old et al.

(10) Patent No.: US 7,803,798 B2
(45) Date of Patent: *Sep. 28, 2010

(54) THERAPEUTIC COMPOUNDS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/427,821

(22) Filed: Apr. 22, 2009

(65) Prior Publication Data

US 2009/0270386 A1    Oct. 29, 2009

Related U.S. Application Data

(60) Provisional application No. 61/047,726, filed on Apr. 24, 2008.

(51) Int. Cl.
*A61K 31/381* (2006.01)
*A61K 31/5377* (2006.01)
*C07D 411/12* (2006.01)
*C07D 333/22* (2006.01)

(52) U.S. Cl. .................... 514/231.5; 514/438; 544/146; 549/71

(58) Field of Classification Search .................... None
See application file for complete search history.

(56) References Cited

U.S. PATENT DOCUMENTS

| 6,437,146 | B1 | 8/2002 | Hattori et al. |
| 6,710,072 | B2 | 3/2004 | Burk et al. |
| 7,091,231 | B2 | 8/2006 | Donde et al. |
| 7,507,817 | B2 * | 3/2009 | Old et al. ..................... 544/106 |
| 2009/0270385 | A1 * | 10/2009 | Old et al. .................. 514/231.5 |

FOREIGN PATENT DOCUMENTS

| WO | WO 2007/115020 | 10/2007 |
| WO | WO 2007/131012 | 11/2007 |
| WO | WO 2007/149829 | 12/2007 |
| WO | WO 2008/091860 | 7/2008 |

OTHER PUBLICATIONS

U.S. Appl. No. 12/523,409, filed Jul. 2009, Old et al.*
U.S. Appl. No. 60/757,696, filed Jan. 10, 2006, Old.
U.S. Appl. No. 60/805,285, filed Jun. 20, 2006, Old.
Carey, Francis A.: Organic Chemistry, New York: McGraw-Hill Book Company 1987, p. 63.

* cited by examiner

*Primary Examiner*—Kamal A Saeed
*Assistant Examiner*—Michael Barker
(74) *Attorney, Agent, or Firm*—Kevin J. Forrestal; John E. Wurst; Doina G. Ene

(57) ABSTRACT

Compounds comprising

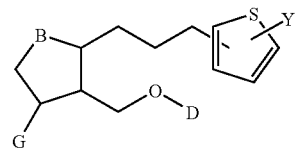

or a pharmaceutically acceptable salt or a prodrug thereof, are disclosed, wherein G, B, D, and Y are as described.

Methods, compositions, and medicaments related thereto are also disclosed.

10 Claims, No Drawings

THERAPEUTIC COMPOUNDS

RELATED APPLICATION

This application claims the benefit of U.S. Provisional Application Ser. No. 61/047,726, filed Apr. 24, 2008, the disclosure of which is hereby incorporated in its entirety herein by reference

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

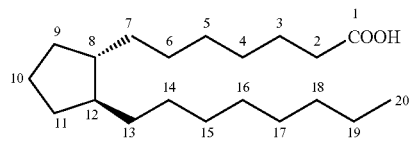

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

Disclosed herein is a compound of the formula

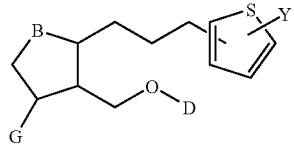

or a pharmaceutically acceptable salt or a prodrug thereof;

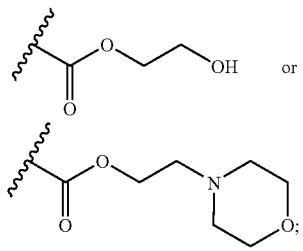

wherein Y is

B is C=O, CH$_2$, CHOH, CHCl, CHF, CHBr, or CHCN;

G is OH or H; and

D is substituted phenyl.

These compounds have several chiral centers. While all stereoisomers are contemplated herein, those shown below are believed to be particularly useful.

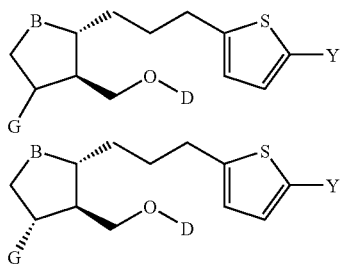

As used herein, substituted phenyl refers to phenyl having one or more substituents. The substituents of phenyl have from 0 to 6 carbon atoms, from 0 to 3 atoms independently selected from O, S, N, F, Cl, Br, or I, and from 0 to 15 hydrogen atoms. If a substituent is a salt, such as a carboxylic acid, and it is associated with a counterion, the counterion is not counted as an atom of the substituent. For example, CO$_2^-$ Na$^+$ is treated as having 1 carbon and 2 oxygen atoms. Substituents must be sufficiently stable to be stored in a bottle at room temperature under a normal atmosphere for at least 12 hours, or stable enough to be useful for any purpose disclosed herein. Examples of substituents include, but are not limited to: hydrocarbyl, including alkyl, alkenyl, alkynyl, which are linear, branched, or cyclic, such as methyl, ethyl, propyl isomers, butyl isomers, and the like;

hydrocarbyloxy, including alkoxy, alkenoxy, alkynoxy; such as —OCH$_3$, OEthyl, O-iPropyl; and the like;

acyl, i.e.

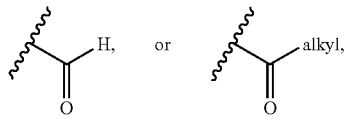

including acetyl, propanyl, and the like;

acyloxy, i.e. —O-acyl, including formate, acetate, propanoate, and the like;

amino, i.e. NH$_2$, NH(hydrocarbyl), or N(hydocarbyl)$_2$;

hydroxylalkyl, meaning alkyl having one or more hydroxyl groups, such as CH$_2$OH, CH$_2$CH$_2$OH, and the like;

CF$_3$;

F;

Cl;

Br;

I;

CN;

NO$_2$;

SO$_3$H, and/or

OH.

Substituents on phenyl may be the same or different.

In one embodiment, phenyl has 1, 2, or 3 substituents.

In another embodiment, at least one substituent is C$_{1-3}$ alkyl, Cl, or F.

In another embodiment, all substituents are C$_{1-3}$ alkyl, Cl, F, or hydroxyalkyl.

Compounds of the following structures are specifically contemplated as individual embodiments.

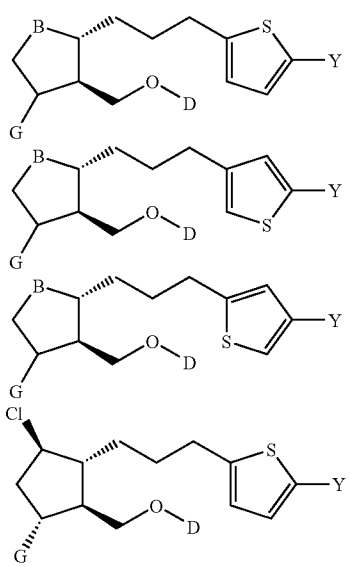

-continued

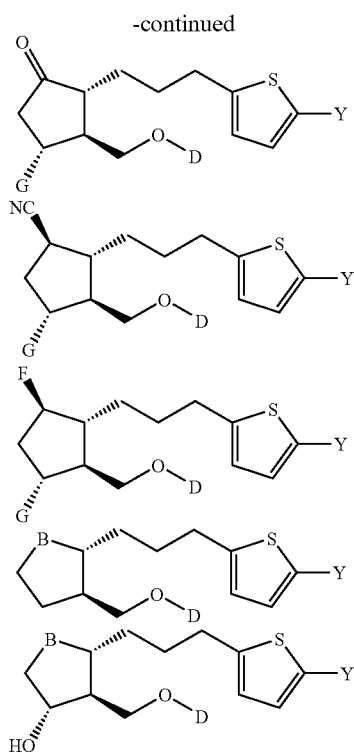

These compounds are useful for treating glaucoma and elevated intraocular pressure.

For the purposes of this disclosure, "treat," "treating," or "treatment" refer to the use of a compound, composition, therapeutically active agent, or drug in the diagnosis, cure, mitigation, treatment, prevention of disease or other undesirable condition.

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiogicla acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without anti oxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Synthetic Methods

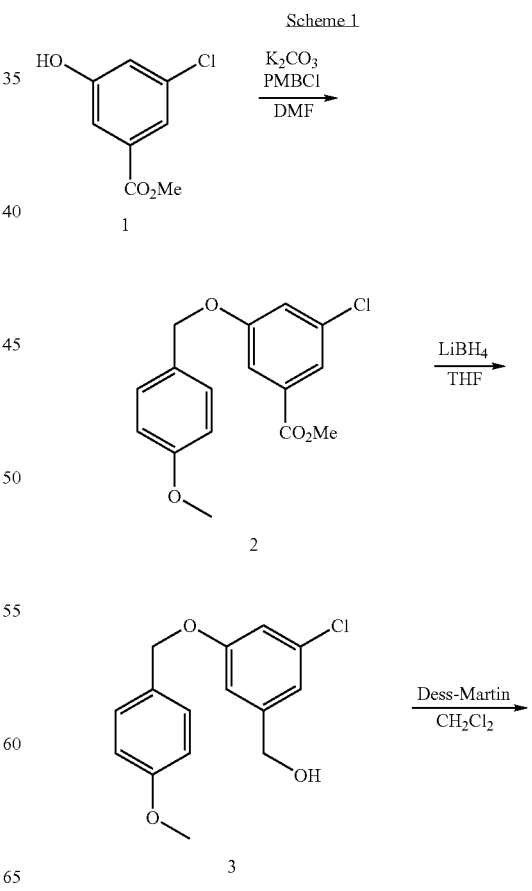

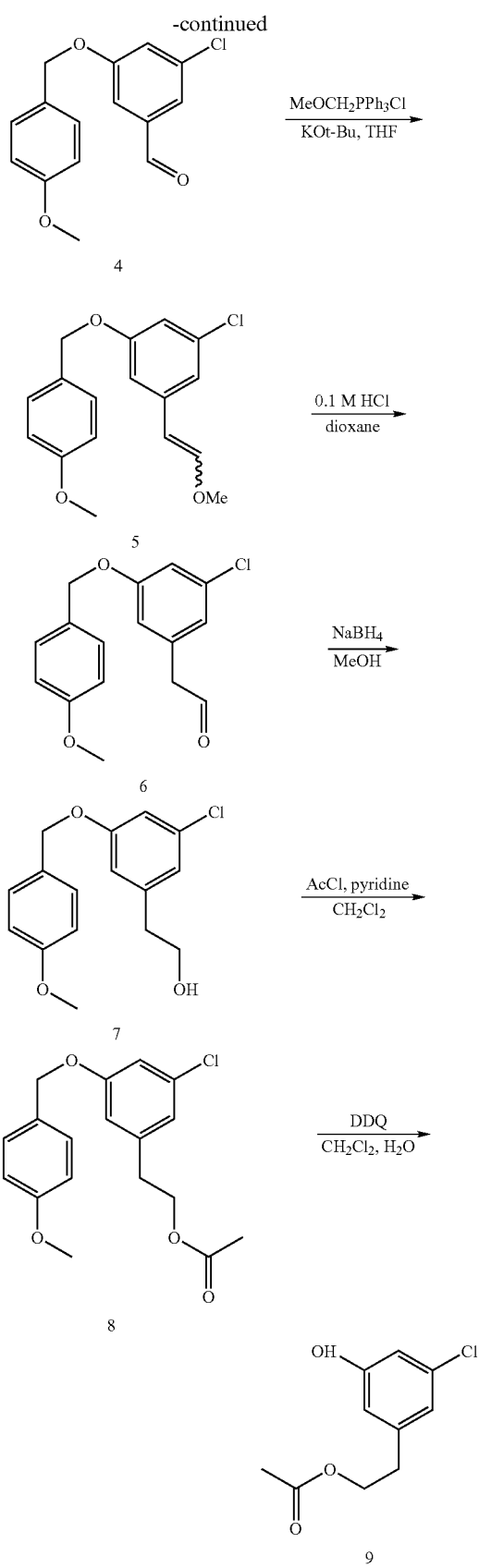

Step 1. Protection of Phenol 1 to Give Ether 2

Potassium carbonate (4.3 g, 31.1 mmol) and 4-methoxybenzyl chloride (2.02 mL, 14.9 mmol) were added to a solution of phenol 1 (see U.S. Provisional Patent Application No. 60/757,696, filed Jan. 10, 2006, incorporated by reference herein, 2.30 g, 12.3 mmol) in DMF (100 mL). The mixture was heated at 100° C. After 3 hours the mixture was allowed to cool to room temperature and then partitioned between water (150 mL) and EtOAc (200 mL). The phases were separated and the organic phase was washed with additional water (100 mL) and brine (50 mL). The organic phase was then dried ($MgSO_4$), filtered and concentrated in vacuo. Purification of the residue by flash column chromatography on silica gel (20% EtOAc/hexane) afforded 3.25 g (86%) of ether 2.

Step 2. Reduction of 2 to Give 3

A solution of ester 2 (3.25 g, 10.6 mmol) in THF (17 mL) was added via syringe to a solution of $LiBH_4$ (0.346 g, 15.9 mmol) in THF (5 mL) at 0° C. The mixture was heated at 80° C. overnight. The reaction mixture was allowed to cool to room temperature, quenched with water, diluted with 5% aqueous citric acid (100 mL) and extracted with EtOAc (75 mL). The organic phase was dried ($MgSO_4$), filtered and concentrated in vacuo. Purification of the crude residue by flash column chromatography on silica gel (30% EtOAc/hexane) afforded 2.91 g (99%) of alcohol 3.

Step 3. Oxidation of 3 to Give 4

A solution of alcohol 3 (2.50 g, 8.97 mmol) in $CH_2Cl_2$ (125 mL) was added to a solution of Dess-Martin periodinane (4.57 g, 10.8 mmol) in $CH_2Cl_2$ (125 mL). After 2 hours at room temperature the reaction was partitioned between water (500 mL) and $CH_2Cl_2$ (300 mL). The phases were separated and the aqueous phase was extracted with $CH_2Cl_2$ (2×250 mL). The combined organic phase was washed with brine (200 mL) then dried ($MgSO_4$), filtered and concentrated in vacuo. Purification of the crude residue by flash column chromatography on silica gel (30% EtOAc/hexane) afforded 2.42 g (97%) of aldehyde 4.

Step 4. Wittig Reaction of 4 to Give 5

Potassium tert-butoxide (2.54 g, 22.6 mmol) was added to a solution of methoxymethyltriphenylphosphonium chloride (3.72 g, 10.8 mmol) in THF (60 mL) at 0° C. After 30 minutes at 0° C., a solution of aldehyde 4 (2.5 g, 9.03 mmol) in THF (30 mL) was added. The reaction mixture was allowed to warm to room temperature and stirred overnight. The reaction was quenched at 0° C. by the slow addition of $H_2O$ then was partitioned between 10% aqueous HCl (95 mL) and EtOAc (100 mL). The phases were separated and the aqueous phase was extracted with EtOAc (2×50 mL). The combined organic phase was washed with brine (20 mL) then dried ($MgSO_4$), filtered and concentrated in vacuo. Purification of the crude residue by flash column chromatography on silica gel (40% EtOAc/hexane) afforded 2.70 g (98%) of enol ether 5.

Step 5. Hydrolysis of 5 to Give 6

M aqueous HCl (2.84 mL, 0.28 mmol) was added to a solution of enol ether 5 (2.70 g, 8.86 mmol) in dioxane (90 mL). After 1 hour at room temperature, the mixture was heated at 60° C. for 2.5 hours then cooled to room temperature. The reaction mixture was partitioned between saturated aqueous $NaHCO_3$ (300 mL) and $CH_2Cl_2$ (300 mL). The phases were separated and the aqueous phase was extracted with $CH_2Cl_2$ (2×300 mL). The combined organic phase was washed with $H_2O$ and brine then dried ($MgSO_4$), filtered and concentrated in vacuo. Purification of the crude residue by flash column chromatography on silica gel (30% EtOAc/hexane) afforded 812 mg (32%) of aldehyde 6.

Step 6. Reduction of 6 to Give 7

Sodium borohydride (159 mg, 4.20 mmol) was added to a solution of aldehyde 6 (812 mg, 2.79 mmol) in MeOH (34 mL) at 0° C. The mixture was allowed to warm to room temperature. After 20 minutes at room temperature, the reaction was cooled to 0° C. and quenched by the slow addition of water. The mixture was then diluted with water (200 mL) and extracted with EtOAc (2×300 mL). The combined organic phase was washed with brine, dried (MgSO$_4$), filtered and concentrated in vacuo. Purification of the crude residue by flash column chromatography on silica gel (50% EtOAc/hexane) afforded 816 mg (99%) of alcohol 7.

Step 7. Protection of 7 to Give 8

Pyridine (247 µL, 3.05 mmol) and acetyl chloride (216 µL, 3.04 mmol) were added sequentially to a solution of alcohol 7 (816 mg, 2.79 mmol) in CH$_2$Cl$_2$ (15 mL). After 5 min, the reaction mixture was partitioned between saturated aqueous NaHCO$_3$ (150 mL) and CH$_2$Cl$_2$ (150 mL). The phases were separated and the aqueous phase was extracted with CH$_2$Cl$_2$ (2×150 mL). The combined organic phases were washed with brine (150 mL), dried (MgSO$_4$), filtered and concentrated in vacuo. Purification of the crude residue by flash column chromatography on silica gel (10% EtOAc/hexane) afforded 850 mg (91%) of acetate 8.

Step 8. Deprotection of 8 to Give 9

2,3-Dichloro-5,6-dicyano-1,4-benzoquinone (DDQ, 814 mg, 3.59 mmol) was added to a mixture of ether 8 (400 mg, 1.19 mmol) in CH$_2$Cl$_2$ (9 mL) and H$_2$O (0.45 mL) at 0° C. After 1 hour at 0° C. the reaction was allowed to warm to room temperature. After 4 hours at room temperature, the reaction was quenched with saturated aqueous NaHCO$_3$ (100 mL). The mixture was extracted with CH$_2$Cl$_2$ (3×100 mL). The combined extracts were washed with water and brine then dried (MgSO$_4$), filtered and concentrated in vacuo. Purification of the residue by flash column chromatography on silica gel (30% EtOAc/hexane) afforded 80 mg (31%) of compound 9.

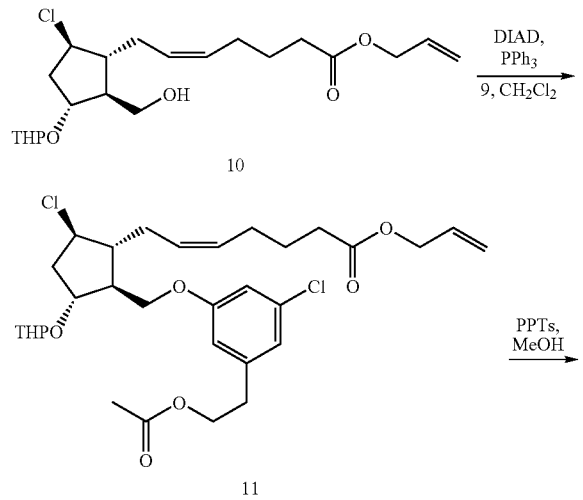

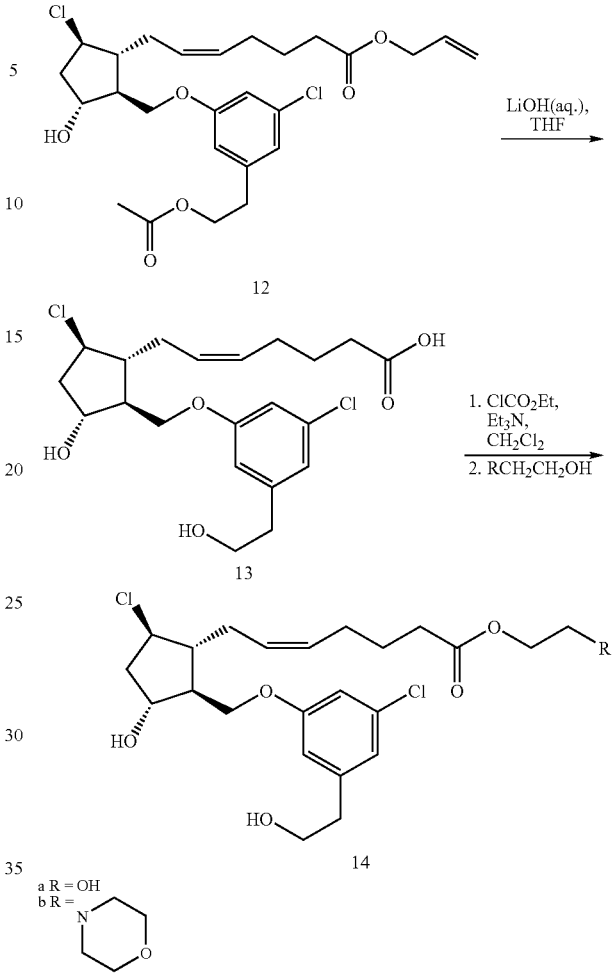

Step 1. Mitsunobu Reaction of 9 and 10 to Give 11

Triphenylphosphine (98 mg, 0.37 mmol) and diisopropyl azodicarboxylate (DIAD, 58 µL, 0.30 mmol) were added sequentially to a solution of alcohol 10 (see U.S. Provisional Patent Application No. 60/757,696, filed Jan. 10, 2006; 100 mg, 0.25 mmol) and phenol 9 (preparation 1, 80 mg, 0.37 mmol) in CH$_2$Cl$_2$ (1.0 mL). After stirring 18 hours at room temperature, the reaction mixture was partitioned between saturated aqueous NaHCO$_3$ (20 mL) and CH$_2$Cl$_2$ (15 mL). The phases were separated and the aqueous phase was extracted with CH$_2$Cl$_2$ (2×20 mL). The combined organic phase was washed with brine (15 mL), dried (MgSO$_4$), filtered and concentrated in vacuo. Purification of the residue by flash column chromatography on silica gel (20% EtOAc/hexane) afforded 108 mg (72%) of aryl ether 11.

Step 2: Deprotection of 11 to Give 12.

Pyridinium p-toluenesulfonate (PPTs, 4.7 mg, 0.019 mmol) was added to a solution of 11 (108 mg, 0.18 mmol) in methanol (2.0 mL) at room temperature under nitrogen. The solution was heated at 40° C. for 5 h, then cooled and concentrated in vacuo. Purification of the crude residue by flash column chromatography on silica gel (50% EtOAc/hexane) afforded 53 mg (57%) of alcohol 12.

Step 3: Hydrolysis of 12 to Give 13

Lithium hydroxide (0.15 mL of a 1.0 M aqueous solution, 0.15 mmol) was added to a solution of ester 12 (13 mg, 0.025 mmol) in THF (0.13 mL). After 2 hours room temperature, the reaction was partitioned between 10% aqueous HCl (3 mL) and EtOAc (7 mL). The phases were separated and the aqueous phase was extracted with EtOAc (2×7 mL). The combined organic phase was washed with brine, dried ($MgSO_4$), filtered and concentrated in vacuo to afford 11 mg (quant.) of compound 13.

Step 4: 13 to Give 14a and 14b

Compound 14a. Triethylamine and ethyl chloroformate are added sequentially to a solution of compound 13 in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 14a.

Compound 14b. Triethylamine and ethyl chloroformate are added sequentially to a solution of compound 13 in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 14b.

-continued

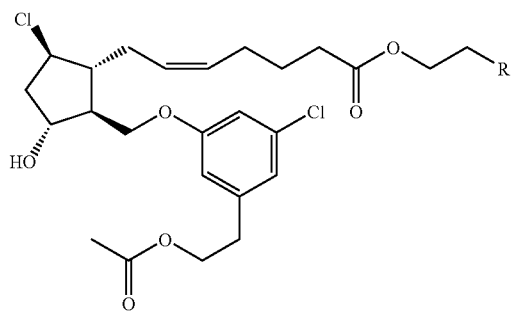

16 a R = OH
b R = 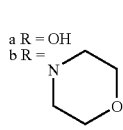

Tetrakis(triphenylphosphine)palladium(0) (20 mg, 0.017 mmol) and pyrrolidine (14 μL, 0.17 mmol) were added sequentially to a solution of allyl ester 12 (30 mg, 0.058 mmol) in $CH_2Cl_2$ (1.0 mL). After 5 min the reaction mixture was partitioned between 1.0 M aqueous HCl (5 mL) and $CH_2Cl_2$ (15 mL). The phases were separated and the aqueous phase was extracted with $CH_2Cl_2$ (2×10 mL). The combined extracts were washed with brine (10 mL), dried ($MgSO_4$), filtered and concentrated in vacuo. Purification of the crude residue by flash column chromatography on silica gel (60% EtOAc/hexane) afforded 9 mg (33%) of compound 15. Compound 16a and 16b can be made according to Step 4 of Scheme 2.

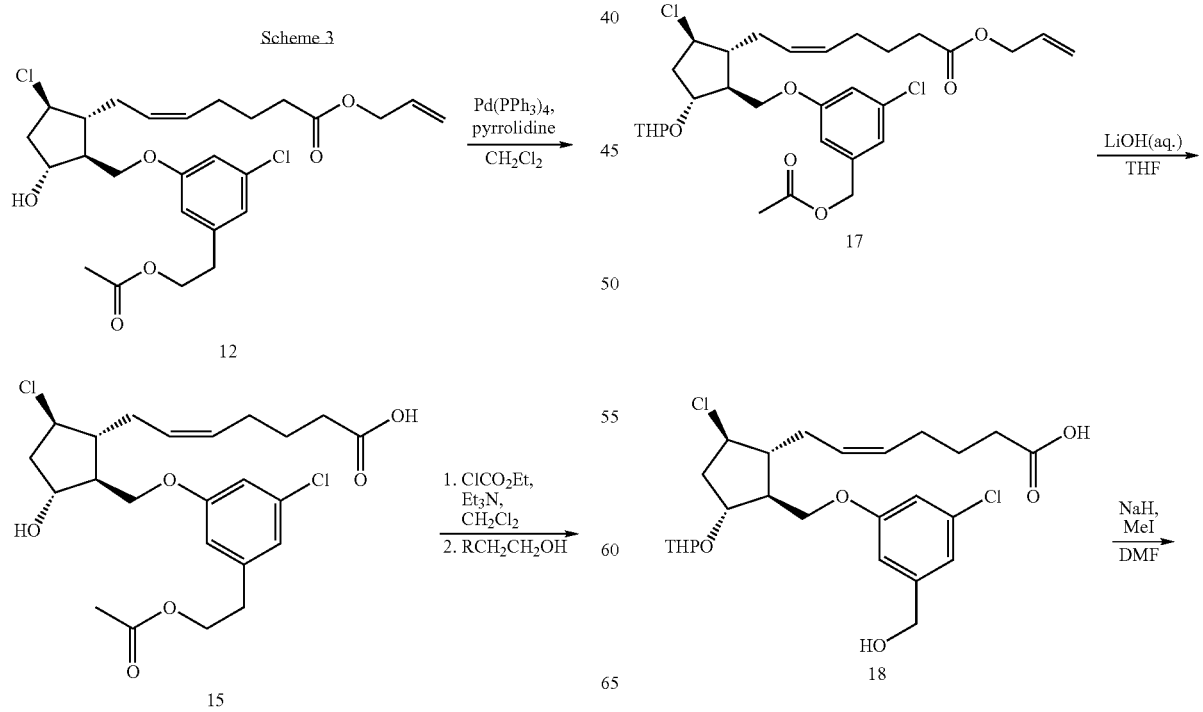

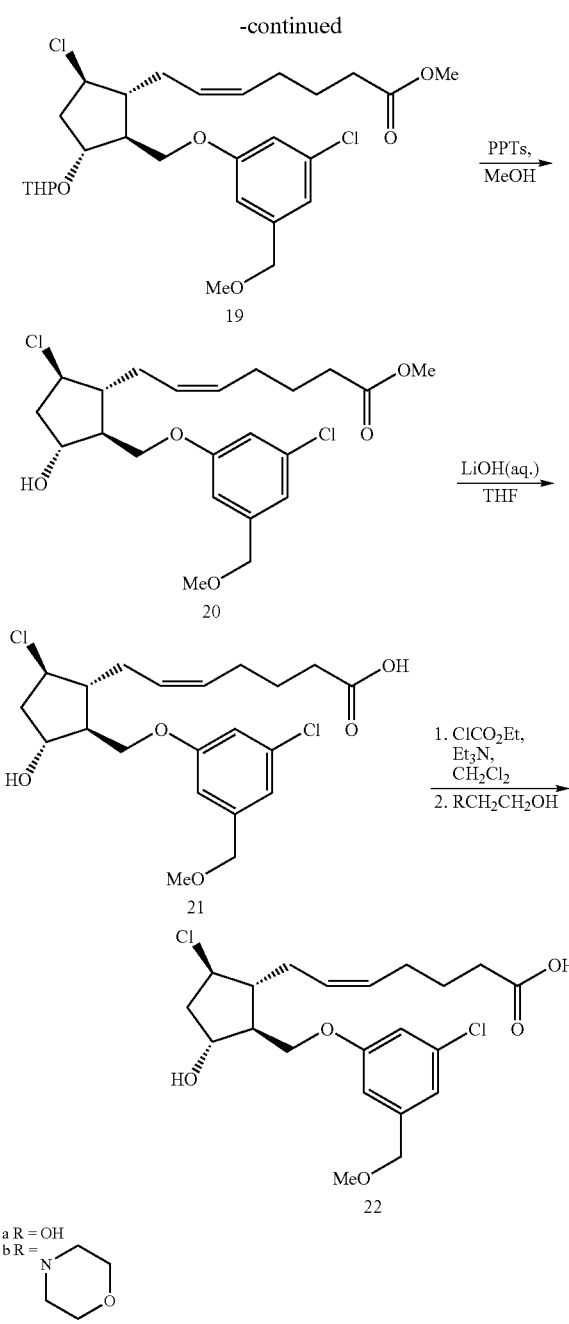

a R = OH
b R = [morpholine]

filtered and concentrated in vacuo. Purification of the crude residue by flash column chromatography on silica gel (hexanes→EtOAc, gradient) afforded 50 mg (88%) of 19.

Step 3. Deprotection of 19 to Give 20

Acetal 19 (50 mg, 0.094 mmol) was converted into 23 mg (55%) of alcohol 20 in accordance with the procedure of Scheme 2, step 2.

Step 4. Hydrolysis of 20 to Give 21

Ester 20 (23 mg, 0.052 mmol) was converted into 13 mg (58%) of compound in accordance with the procedure of Scheme 2, step 3.

Step 5. 21 to give 22a and 22b

Compound 21 can be converted to compounds 16a and 16b according to Step 4 of Scheme 2.

Scheme 5

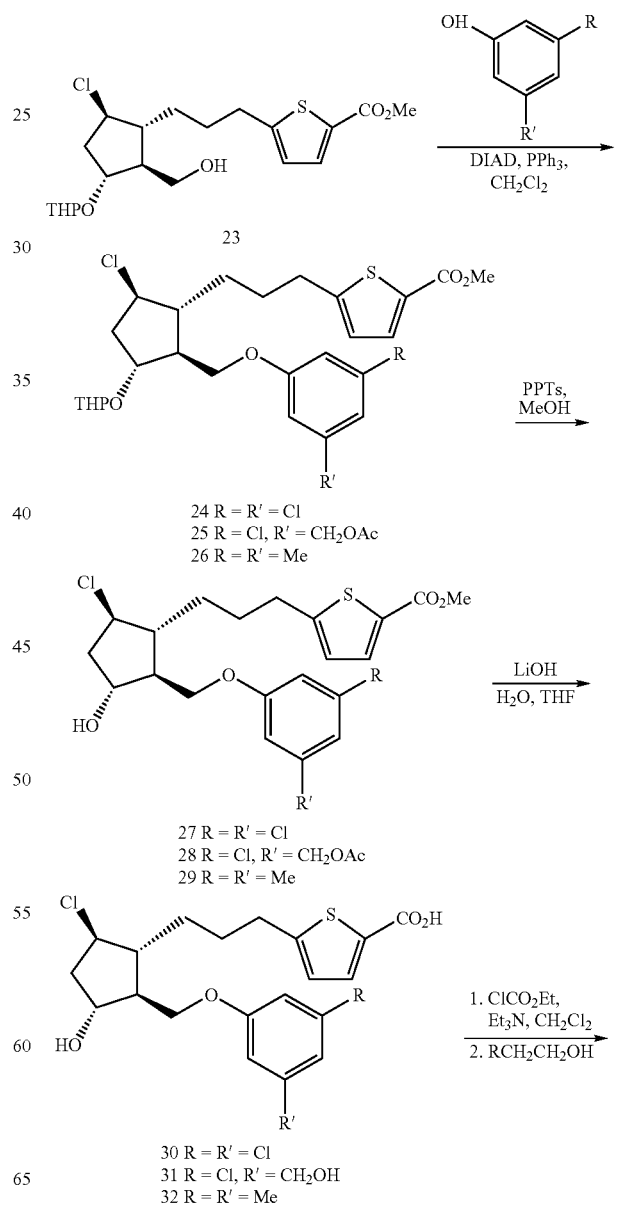

24 R = R' = Cl
25 R = Cl, R' = CH$_2$OAc
26 R = R' = Me

27 R = R' = Cl
28 R = Cl, R' = CH$_2$OAc
29 R = R' = Me

30 R = R' = Cl
31 R = Cl, R' = CH$_2$OH
32 R = R' = Me

Step 1. Hydrolysis of 17 to Give 18

Ester 17 (see U.S. Provisional Patent Application No. 60/757,696, filed Jan. 10, 2006; 200 mg, 0.343 mmol) was converted into 140 mg (57%) of hydroxy-acid 18 in accordance with the procedure of Scheme 2, step 3.

Step 2. Dimethylation of 18 to Give 19

A solution of hydroxy-acid 18 (54 mg, 0.11 mmol) in DMF (0.5 mL) was added to a suspension of sodium hydride (11 mg of a 60 wt. % suspension, 0.28 mmol) in DMF (0.5 mL). Iodomethane (67 μL, 1.08 mmol) was then added. The reaction mixture was partitioned between water (5 mL) and EtOAc (10 mL). The phases were separated and the aqueous phase was extracted with EtOAc (2×10 mL). The combined extracts were washed with brine (10 mL), dried (MgSO$_4$),

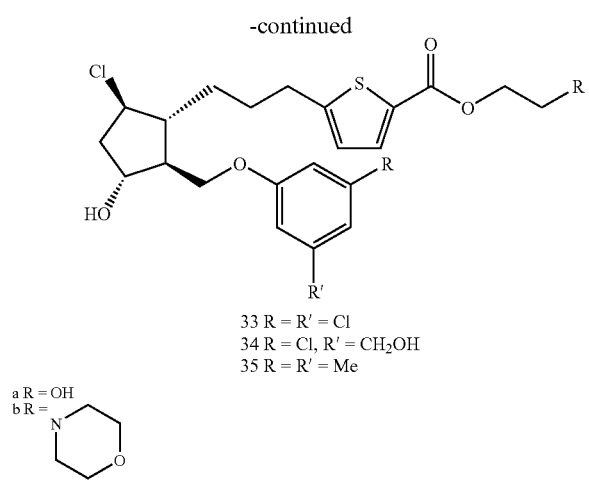

33 R = R' = Cl
34 R = Cl, R' = CH₂OH
35 R = R' = Me a R = OH
b R = [morpholine]

Step 1. Mitsunobu Reaction of 23 to Give 24

Triphenylphosphine (38 mg, 0.14 mmol) and DIAD (23 µL, 0.12 mmol) were added to a solution of alcohol 23 (see U.S. Provisional Patent Application No. 60/805,285, filed Jun. 20, 2006, incorporated by reference herein; 40 mg, 0.096 mmol) and 3,5-dichlorophenol (23 mg, 0.14 mmol) in CH₂Cl₂ (1.0 mL). After stirring 18 hours at room temperature, the mixture was partitioned between CH₂Cl₂ (10 mL) and saturated aqueous NaHCO₃ (10 mL). The phases were separated and the aqueous phase was extracted with CH₂Cl₂ (2×10 mL). The combined organic phase was washed with brine (10 mL), dried (MgSO₄), filtered and concentrated in vacuo. Purification of the residue by flash column chromatography on silica gel (hexane→EtOAc, gradient) afforded 20 mg (37%) of 24.

Step 2. Deprotection of 24 to Give 27

Pyridinium p-toluenesulfonate (PPTs, 1 mg, 0.004 mmol) was added to a solution of 24 (20 mg, 0.036 mmol) in methanol (0.35 mL) at room temperature. The solution was heated at 40° C. overnight, then cooled and concentrated in vacuo. Purification of the crude residue by flash column chromatography on silica gel (hexane→EtOAc, gradient) afforded 10 mg (59%) of 27.

Step 3. Hydrolysis of 27 to Give 30

Ester 27 (10 mg, 0.021 mmol) was converted into 3 mg (31%) of compound 30 in accordance with the procedure of Scheme 2, step 3 with the following modifications: the reaction was stirred for 18 hours at room temperature, and the crude product was purified by flash column chromatography on silica gel (10% MeOH/CH₂Cl₂).

Step 4. 30 to give 33a and 33b

Compound 30 can be converted to compounds 33a and 33b according to Step 4 of Scheme 2.

Step 1.

Ester 28 (see U.S. Provisional Patent Application No. 60/805,285, filed Jun. 20, 2006; 30 mg, 0.058 mmol) was converted into 13 mg (49%) of compound 31 in accordance with the procedure of Scheme 5, step 3 (above).

Step 2. 31 to Give 34a and 34b

Compound 31 can be converted to compounds 34a and 34b according to Step 4 of Scheme 2.

Step 1. Mitsunobu Reaction of 23 to Give 26

Triphenylphosphine (47 mg, 0.18 mmol) and DIAD (27 µL, 0.14 mmol) were added to a solution of alcohol 23 (see U.S. Provisional Patent Application No. 60/805,285, filed Jun. 20, 2006; 50 mg, 0.12 mmol) and 3,5-dimethylphenol (17 mg, 0.14 mmol) in CH₂Cl₂ (0.6 mL). After stirring 18 hours at room temperature, the mixture was partitioned between CH₂Cl₂ (10 mL) and saturated aqueous NaHCO₃ (10 mL). The phases were separated and the aqueous phase was extracted with CH₂Cl₂ (2×10 mL). The combined organic phase was washed with brine (10 mL), dried (MgSO₄), filtered and concentrated in vacuo. Purification of the residue by flash column chromatography on silica gel (hexane→EtOAc, gradient) afforded 53 mg (85%) of 26.

Step 2. Deprotection of 26 to Give 29

Acetal 26 (53 mg, 0.10 mmol) was converted into 37 mg (83%) of alcohol 29 in accordance with the procedure of Scheme 5, step 2 (above).

Step 3. Hydrolysis of 29 to give 32

Ester 29 (37 mg, 0.085 mmol) was converted into 15 mg (42%) of compound 32 in accordance with the procedure of Scheme 2, step 3 with the following modifications: the reaction was stirred for 18 hours at 40° C., and the crude product was purified by flash column chromatography on silica gel (10% MeOH/CH₂Cl₂).

Step 4. 32 to Give 35a and 35b

Compound 32 can be converted to compounds 35a and 35b according to Step 4 of Scheme 2.

Scheme 6

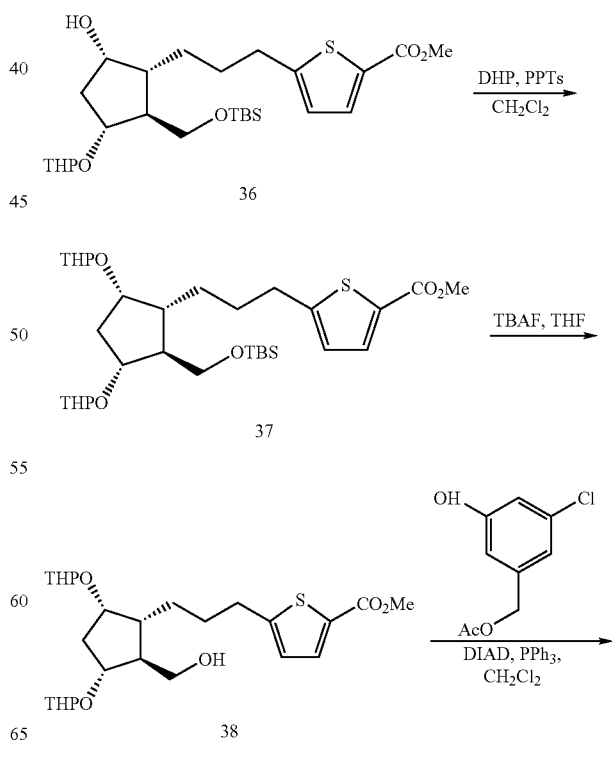

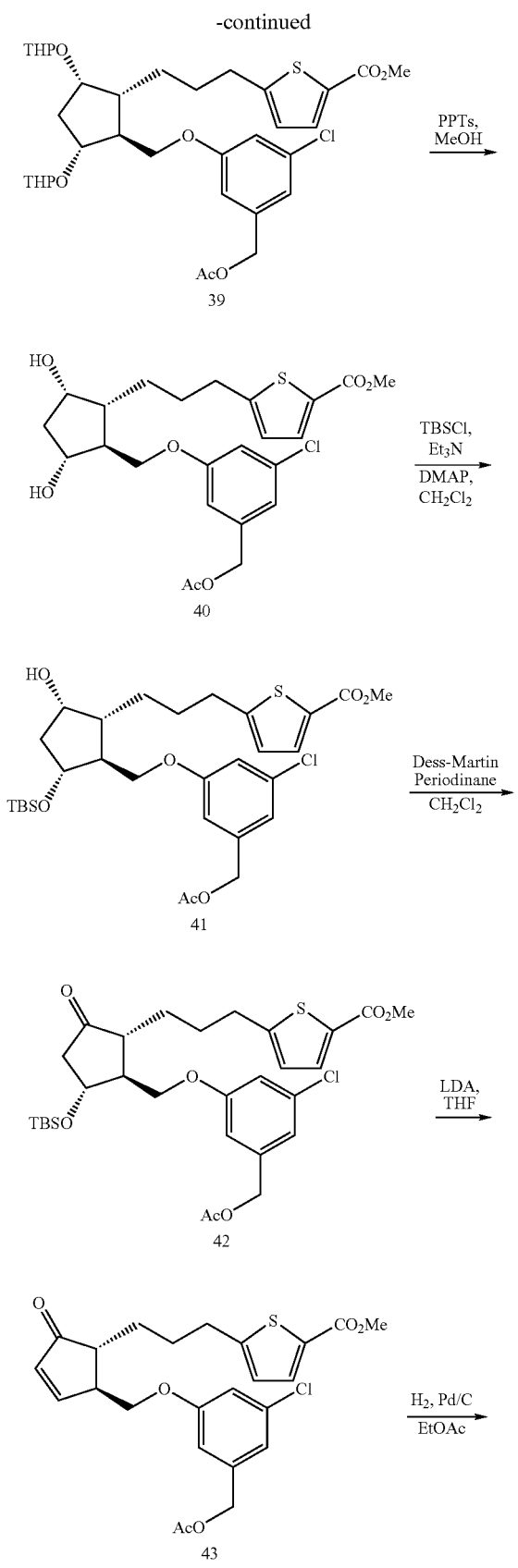
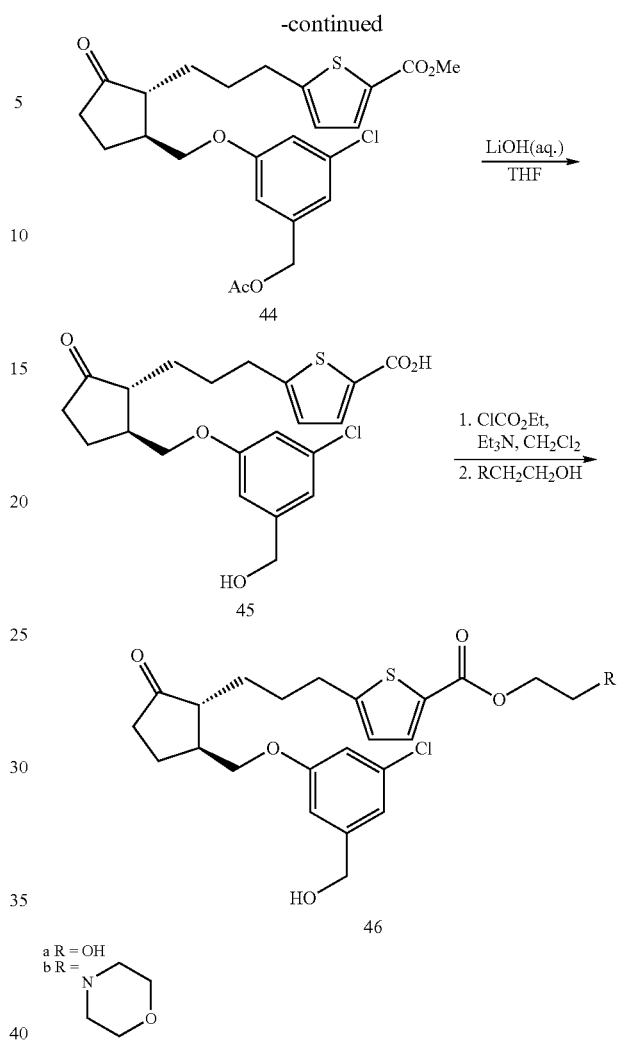

Step 1. Protection of 36 to Give 37

Dihydropyran (391 μL, 4.29 mmol) and PPTs (50 mg, 0.20 mmol) were added to a solution of alcohol 37 (see U.S. Provisional Patent Application No. 60/805,285, filed Jun. 20, 2006; 550 mg, 1.07 mmol) in CH$_2$Cl$_2$ (3.0 mL). The reaction mixture was heated at 40° C. overnight, then cooled and concentrated in vacuo. Purification of the crude residue by flash column chromatography on silica gel (hexane→EtOAc, gradient) afforded 550 mg (86%) of 37.

Step 2. Desilylation of 37 to Give 38

Tetrabutylammonium fluoride (2.51 mL of a 1.0 M THF solution, 2.51 mmol) was added to a solution of 37 (500 mg, 0.84 mmol) in THF (7.6 mL). After 18 hours at room temperature, the reaction mixture was partitioned between water (10 mL) and EtOAc (20 mL). The phases were separated and the aqueous phase was extracted with EtOAc (2×10 mL). The combined extracts were washed with brine then dried (MgSO$_4$), filtered and concentrated in vacuo. Purification of the crude residue by flash column chromatography on silica gel (hexane→EtOAc, gradient) afforded 393 mg (97%) of 38.

Step 3. Mitsunobu of 38 to Give 39

Alcohol 38 (437 mg, 0.91 mmol) and 3-chloro-5-hydroxybenzyl acetate (see U.S. Provisional Patent Application No. 60/757,696, filed Jan. 10, 2006; 218 mg, 1.09 mmol) were converted into 350 mg (58%) of aryl ether 39 in accordance with the procedure of Scheme 5, step 1.

Step 4. Deprotection of 39 to Give 40

Bis-acetal 39 (350 mg, 0.53 mmol) was converted into 150 mg (57%) of diol 40 in accordance with the procedure of Scheme 5, step 2.

Step 5. Monosilylation of 40 to Give 41

Triethylamine (63 µL, 0.45 mmol), dimethylaminopyridine (7 mg, 0.057 mmol), and tert-butyldimethylsilyl chloride (50 mg, 0.33 mmol) were sequentially added to a solution of 41 (150 mg, 0.30 mmol) in CH$_2$Cl$_2$ (1.5 mL). After stirring 18 hours at room temperature, the mixture was partitioned between CH$_2$Cl$_2$ (10 mL) and saturated aqueous NaHCO$_3$ (5 mL). The phases were separated and the aqueous phase was extracted with CH$_2$Cl$_2$ (2×10 mL). The combined organic phase was washed with brine (10 mL), dried (MgSO$_4$), filtered and concentrated in vacuo. Purification of the residue by flash column chromatography on silica gel (hexane→EtOAc, gradient) afforded 90 mg (49%) of 41.

Step 6. Oxidation of 41 to Give 42

Dess-Martin periodinane (75 mg, 0.18 mmol) was added to a solution of 41 (90 mg, 0.15 mmol) in CH$_2$Cl$_2$ (7.35 mL) at 0° C. and the mixture was allowed to warm to room temperature. After 2 hours at room temperature, the mixture was partitioned between CH$_2$Cl$_2$ (10 mL) and water (10 mL). The phases were separated and the aqueous phase was extracted with CH$_2$Cl$_2$ (2×10 mL). The combined organic phase was washed with brine (5 mL), dried (MgSO$_4$), filtered and concentrated in vacuo. Purification of the residue by flash column chromatography on silica gel (hexane→EtOAc, gradient) afforded 80 mg (89%) of ketone 42.

Step 7. Elimination of 42 to Give 43

A solution of lithium diisopropylamide (0.41 mL of a 2.0 M solution in heptane-THF-ethylbenzene, 0.82 mmol) was added to a solution of 42 (80 mg, 0.13 mmol) in THF (2.3 mL) at −78° C. After 90 minutes at −78° C., the mixture was allowed to warm to room temperature. After 15 minutes at room temperature, the reaction was quenched by the addition of 0.1 N aqueous HCl (15 mL), and extracted with EtOAc (3×20 mL). The combined extracts were washed with brine, dried (MgSO$_4$), filtered and concentrated in vacuo. Purification of the residue by flash column chromatography on silica gel (hexane→EtOAc, gradient) afforded 40 mg (64%) of enone 43.

Step 8. Hydrogenation of 43 to Give 44

Palladium on carbon (10 wt. %, 8 mg) was added to a solution of enone 43 (40 mg, 0.084 mmol) in EtOAc (1.6 mL). A hydrogen atmosphere was established by evacuating and refilling with hydrogen (5×) and the reaction mixture was stirred under a balloon of hydrogen for 18 hours. The reaction mixture was filtered through celite, washing with EtOAc, and the filtrate was concentrated in vacuo to afford 31 mg (77%) of saturated ketone 44.

Step 9. Hydrolysis of 44 to Give 45

Ester 44 (5 mg, 0.010 mmol) was converted into 3.5 mg (79%) of compound 45 in accordance with the procedure of Scheme 5, step 3.

Step 10. 45 to Give 46a and 46b

Compound 45 can be converted to compounds 46a and 46b according to Step 4 of Scheme 2.

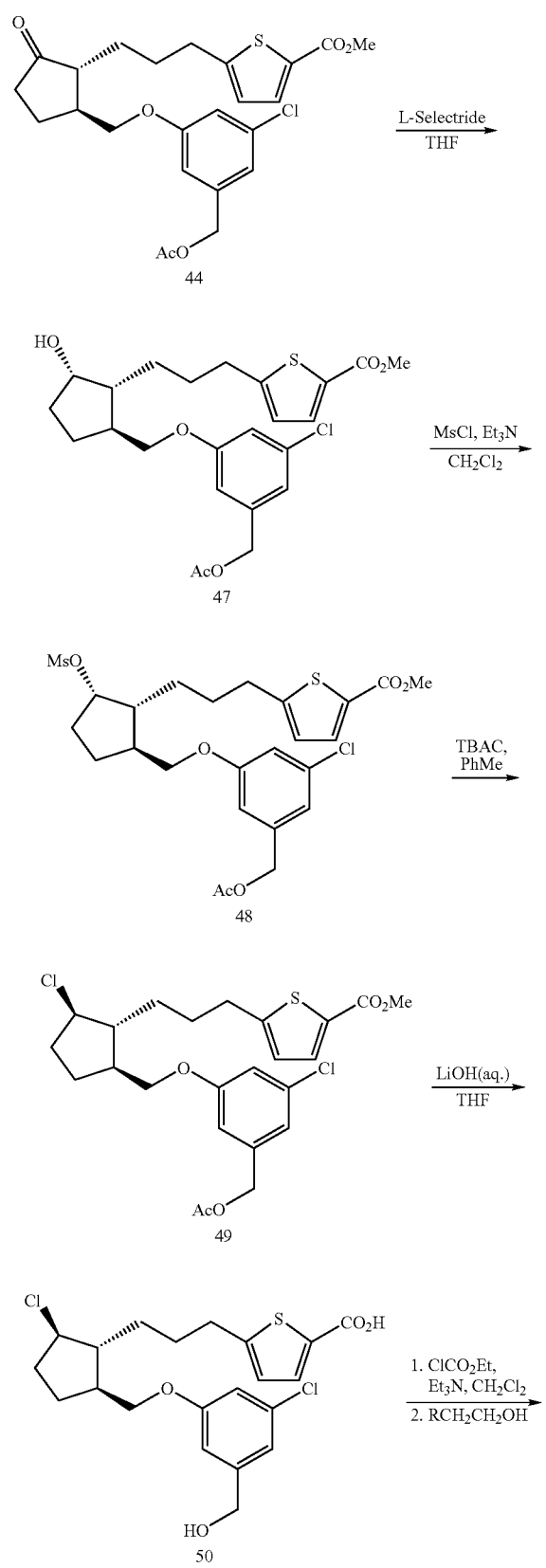

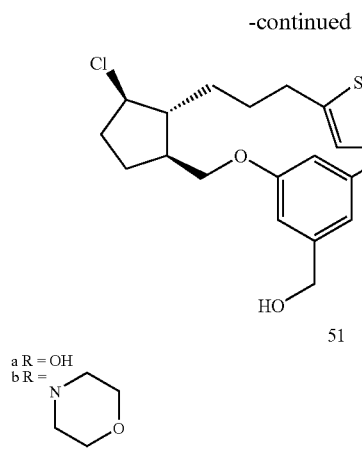

51 a R = OH
b R = <image at line 15>

Scheme 8

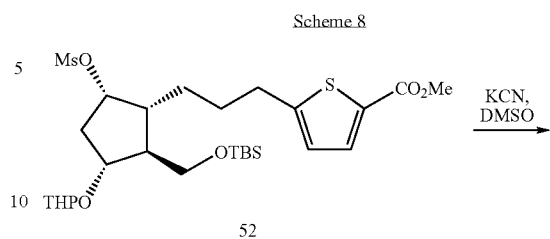

52

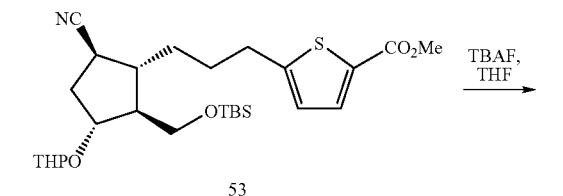

53

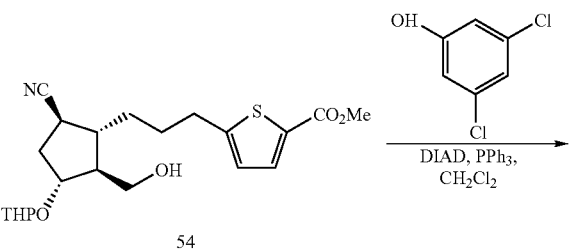

54

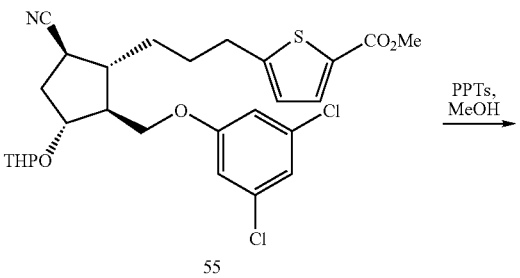

55

Step 1. Reduction of 44 to Give 47

A solution of L-selectride (74 μL of a 1.0 M solution in THF, 0.074 mmol) was added to a solution of 44 (26 mg, 0.054 mmol) in THF (1.8 mL) at −78° C. After 1 hour at −78° C., additional L-selectride (108 μL, 0.108 mmol) was added. After 5 hours at −78° C., the reaction was quenched by the addition of 3% aqueous $H_2O_2$ (1.5 mL) and the mixture was allowed to warm to room temperature. Water (5 mL) was added and the mixture was extracted with EtOAc (2×10 mL). The combined extracts were dried ($MgSO_4$), filtered and concentrated in vacuo. Purification of the residue by flash column chromatography on silica gel (hexane→EtOAc, gradient) afforded 13 mg (50%) of alcohol 47.

Step 2. Mesylation of 47 to Give 48

Triethylamine (5.6 μL, 0.040 mmol) and methanesulfonyl chloride (2.6 μL, 0.033 mmol) were added sequentially to a solution of 47 (13 mg, 0.027 mmol) in $CH_2Cl_2$ (0.2 mL) at 0° C., and reaction was allowed to warm to room temperature. After 18 hours at room temperature, saturated aqueous $NaHCO_3$ (5 mL) was added and the mixture was extracted with $CH_2Cl_2$ (3×5 mL). The combined extracts were washed with brine (2 mL), dried ($MgSO_4$), filtered and concentrated in vacuo to afford 15 mg (99%) of mesylate 48.

Step 3. Conversion of 48 to Chloride 49

Tetrabutylammonium chloride (38 mg, 0.14 mmol) was added to a solution of 48 (15 mg, 0.027 mmol) in toluene (0.27 mL). The reaction mixture was heated at 50° C. for 18 hours. The cooled mixture was diluted with brine (10 mL) and extracted with EtOAc (3×25 mL). The combined organic extracts were dried ($MgSO_4$), filtered and concentrated in vacuo. Purification of the crude residue by flash column chromatography on silica gel (hexane→EtOAc, gradient) afforded 5 mg (37%) of chloride 49.

Step 4. Hydrolysis of 49 to Give 50

Ester 49 (5 mg, 0.010 mmol) was converted into 1 mg (23%) of compound 50 in accordance with the procedure of Scheme 5, step 3.

Step 5. 50 to Give 51a and 51b

Compound 50 can be converted to compounds 51a and 51b according to Step 4 of Scheme 2.

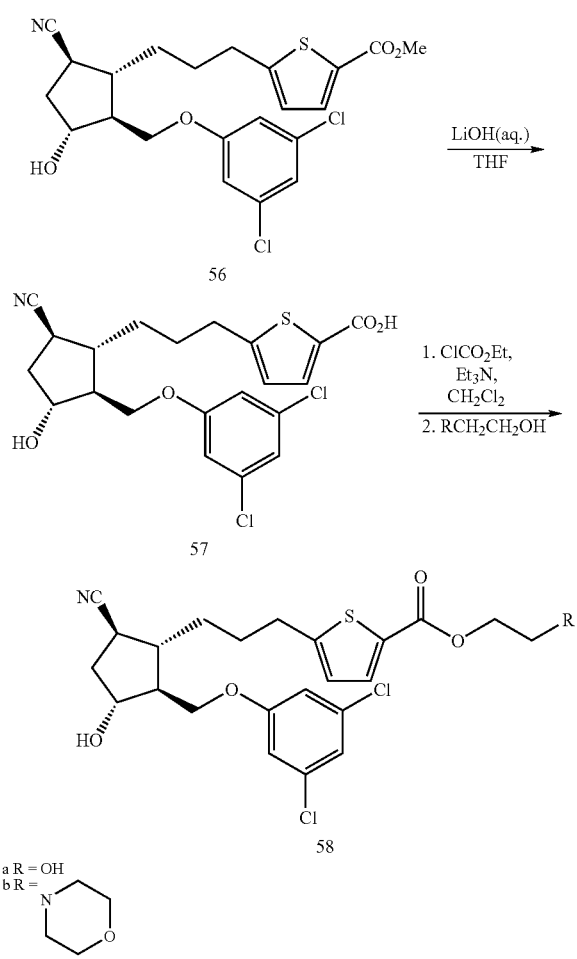

Step 1. Conversion of 52 to Give Nitrile 53

Potassium cyanide (569 mg, 8.74 mmol) was added to a solution of mesylate 52 (see U.S. Provisional Patent Application No. 60/805,285, filed Jun. 20, 2006; 2.10 g, 3.55 mmol) in DMSO (97 mL). The mixture was heated at 65° C. for 18 hours then cooled to room temperature. The mixture was diluted with water (100 mL) and brine (100 mL) and extracted with $CH_2Cl_2$ (3×200 mL). The combined organic phase was dried ($MgSO_4$) filtered and concentrated in vacuo. Purification of the residue by flash column chromatography on silica gel (hexane→EtOAc, gradient) afforded 270 mg (15%) of nitrile 53.

Step 2. Desilylation of 53 to Give 54

Silyl ether 53 (270 mg, 0.52 mmol) was converted into 150 mg (71%) of alcohol 54 in accordance with the procedure of Scheme 6, step 2.

Step 3. Mitsunobu of 54 to Give 55

Alcohol 54 (50 mg, 0.12 mmol) and 3,5-dichlorophenol (24 mg, 0.15 mmol) were converted into 50 mg (74%) of aryl ether 55 in accordance with the procedure of Scheme 5, step 1.

Step 4. Deprotection of 55 to Give 56

Acetal 55 (50 mg, 0.090 mmol) was converted into 20 mg (47%) of alcohol 56 in accordance with the procedure of Scheme 5, step 2.

Step 5. Hydrolysis of 56 to Give 57

Ester 56 (15 mg, 0.032 mmol) was converted into 8 mg (55%) of compound 57 in accordance with the procedure of Scheme 2, step 3 with the following modifications: the concentration was 0.4 M in THF, the reaction was stirred for 18 hours at 40° C., and the crude product was purified by flash column chromatography on silica gel (10% MeOH/$CH_2Cl_2$).

Step 6. 57 to Give 58a and 58b

Compound 57 can be converted to compounds 58a and 58b according to Step 4 of Scheme 2.

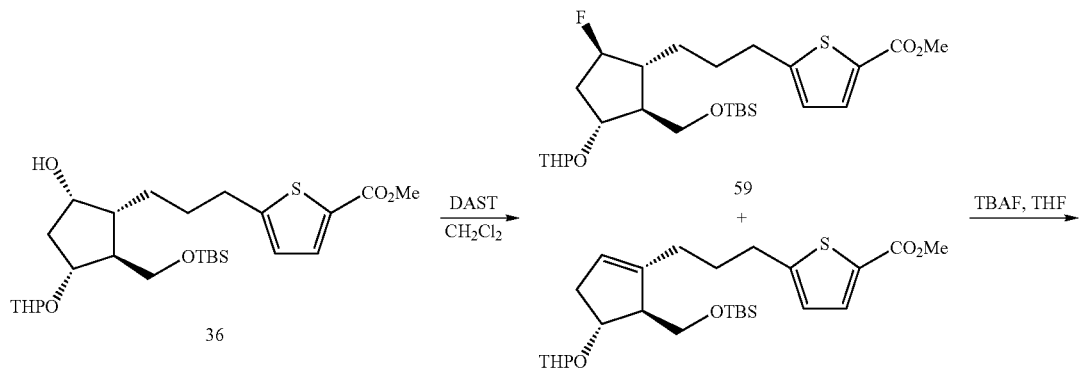

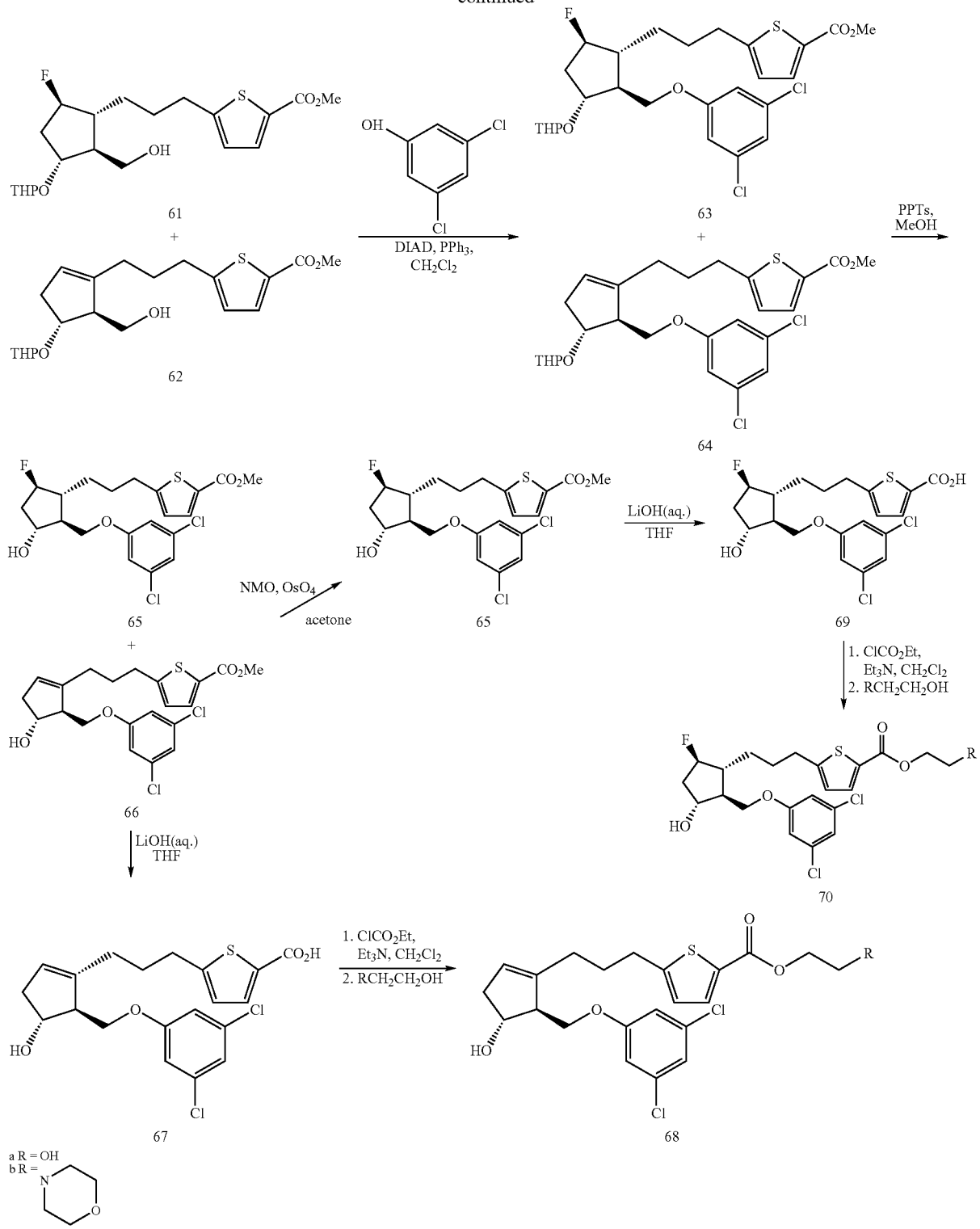

Step 1. Conversion of 36 to Fluoride 59 and Alkene 60

(Diethylamino)sulfur trifluoride (DAST, 104 μL, 0.79 mmol) was added to a solution of alcohol 36 (see U.S. Provisional Patent Application No. 60/805,285, filed Jun. 20, 2006; 200 mg, 0.39 mmol) in CH$_2$Cl$_2$ (92 mL) at −78° C. After 30 minutes at room temperature, the reaction was quenched with saturated aqueous NaHCO$_3$ (25 mL). The mixture was diluted with water (25 mL) and extracted with CH$_2$Cl$_2$ (2×25 mL). The combined organic phase was dried (MgSO$_4$), filtered and concentrated in vacuo. Purification of the residue by flash column chromatography on silica gel (hexane→EtOAc, gradient) afforded 42 mg (~20%) of an inseparable mixture of 59 and 60.

Step 2. Disilylation of 59/60 to 61/62

Silyl ethers 59/60 (42 mg, ~0.08 mmol) were converted into 25 mg (~77%) of inseparable alcohols 61/62 in accordance with the procedure of Scheme 6, step 2.

Step 3. Mitsunobu of 61/62 to 63/64

Alcohols 61/62 (25 mg, ~0.06 mmol) and 3,5-dichlorophenol (9 mg, 0.055 mmol) were converted into 24 mg (~70%) of inseparable aryl ethers 63/64 in accordance with the procedure of Scheme 5, step 1.

Step 4. Deprotection of 63/64 to 65 and 66

Acetals 63/64 (24 mg, ~0.45 mmol) were converted into 1 mg (~5%) of hydroxyl alkene 57 and 20 mg (~83%) of a mixture of 65 and 66 in accordance with the procedure of Scheme 5, step 2.

Step 5. Hydrolysis of 66 to 67

Ester 66 (1 mg, 0.022 mmol) was converted into 1 mg (quant.) of compound 67 in accordance with the procedure of Scheme 5, step 3.

Step 6. 67 to Give 68a and 68b

Compound 67 can be converted to compounds 68a and 68b according to Step 4 of Scheme 2.

Step 1. Oxidation of 66 to Afford Pure 65

Osmium tetroxide (160 μL of a 4 wt. % solution in water, 0.026 mmol) was added to a solution of 4-methylmorpholine N-oxide (NMO, 11.4 mg, 0.097 mmol) and the mixture of 65 and 66 (Scheme 9, step 4, 20 mg, ~0.044 mmol) in acetone (1.1 mL) at 0° C. and the reaction was allowed to warm to room temperature. After 1 h, the reaction was quenched with 5% aqueous $NaHCO_3$ (5 mL) and extracted with EtOAc (3×5 mL). The combined extracts were washed with brine (5 mL), dried ($MgSO_4$), filtered and concentrated in vacuo. Purification of the residue by flash column chromatography on silica gel (hexane→EtOAc, gradient) afforded 5 mg (~24%) of fluoride 65.

Step 2. Hydrolysis of 65 to Give 69

Ester 65 (5 mg, 0.011 mmol) was converted into 2 mg (41%) of compound 69 in accordance with the procedure of Scheme 5, step 3.

Step 3. 69 to Give 70a and 70b

Compound 69 can be converted to compounds 70a and 70b according to Step 4 of Scheme 2.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer." Unless stereochemistry is explicitly depicted, a structure is intended to include every possible stereoisomer, both pure or in any possible mixture. Unless stereochemistry is explicitly depicted, a structure is intended to include every possible stereoisomer, both pure or in any possible mixture.

The following non-limiting examples are compounds that are contemplated according to the present description.

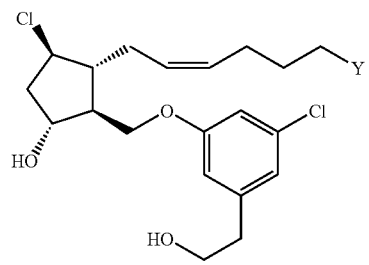

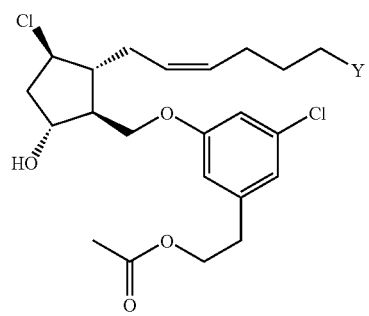

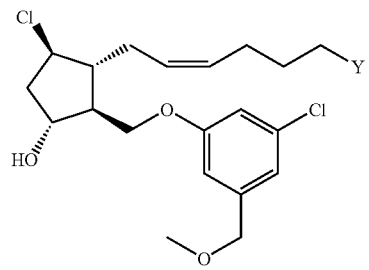

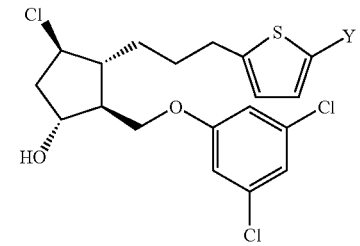

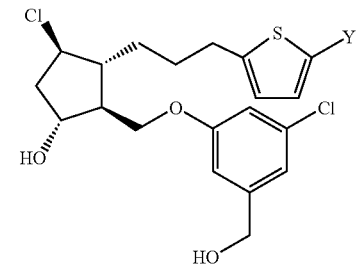

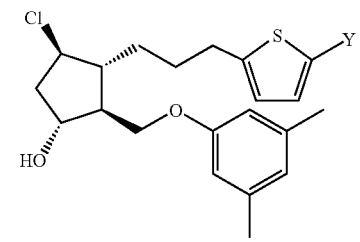

-continued

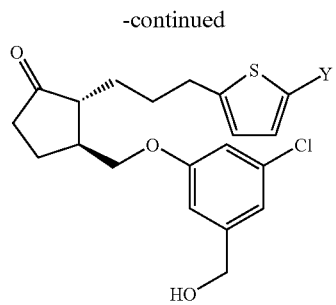

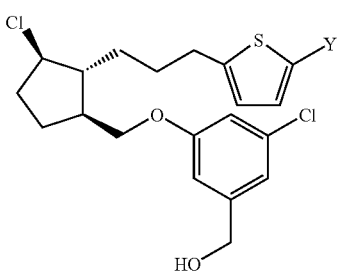

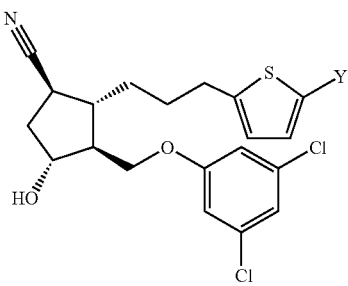

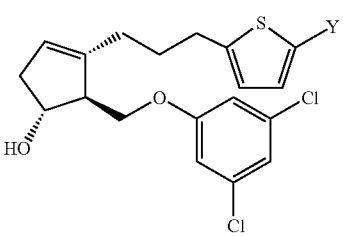

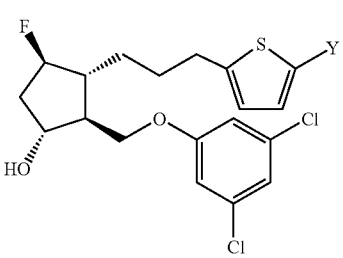

-continued

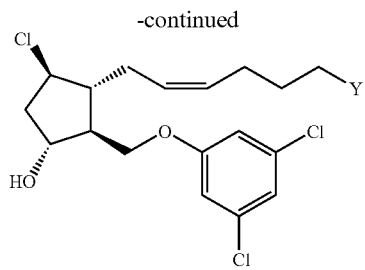

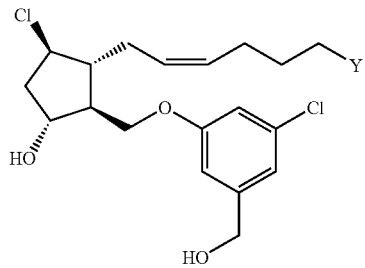

In Vivo Testing

U.S. Pat. No. 7,091,231 describes the methods used for these in vivo tests.

Compounds such as those described in the above are tested in vivo to measure its ability to reduce intraocular pressure. Compound 14a is tested in normotensive dogs. The intraocular pressure (IOP) decreases from baseline. This compound is also tested in laser-induced hypertensive monkeys, the IOP decreases from baseline.

Compound 14b is tested in normotensive dogs. The intraocular pressure (IOP) decreases from baseline. This compound is also tested in laser-induced hypertensive monkeys, the IOP decreases from baseline.

Compound 16a is tested in normotensive dogs. The intraocular pressure (IOP) decreases from baseline. This compound is also tested in laser-induced hypertensive monkeys, the IOP decreases from baseline.

Compound 16b is tested in normotensive dogs. The intraocular pressure (IOP) decreases from baseline. This compound is also tested in laser-induced hypertensive monkeys, the IOP decreases from baseline.

Compound 22a is tested in normotensive dogs. The intraocular pressure (IOP) decreases from baseline. This compound is also tested in laser-induced hypertensive monkeys, the IOP decreases from baseline.

Compound 22b is tested in normotensive dogs. The intraocular pressure (IOP) decreases from baseline. This compound is also tested in laser-induced hypertensive monkeys, the IOP decreases from baseline.

Compound 33a is tested in normotensive dogs. The intraocular pressure (IOP) decreases from baseline. This compound is also tested in laser-induced hypertensive monkeys, the IOP decreases from baseline.

Compound 33b is tested in normotensive dogs. The intraocular pressure (IOP) decreases from baseline. This compound is also tested in laser-induced hypertensive monkeys, the IOP decreases from baseline.

Compound 34a is tested in normotensive dogs. The intraocular pressure (IOP) decreases from baseline. This compound is also tested in laser-induced hypertensive monkeys, the IOP decreases from baseline.

Compound 34b is tested in normotensive dogs. The intraocular pressure (IOP) decreases from baseline. This compound is also tested in laser-induced hypertensive monkeys, the IOP decreases from baseline.

Compound 35a is tested in normotensive dogs. The intraocular pressure (IOP) decreases from baseline. This compound is also tested in laser-induced hypertensive monkeys, the IOP decreases from baseline.

Compound 35b is tested in normotensive dogs. The intraocular pressure (IOP) decreases from baseline. This compound is also tested in laser-induced hypertensive monkeys, the IOP decreases from baseline.

Compound 46a is tested in normotensive dogs. The intraocular pressure (IOP) decreases from baseline. This compound is also tested in laser-induced hypertensive monkeys, the IOP decreases from baseline.

Compound 46b is tested in normotensive dogs. The intraocular pressure (IOP) decreases from baseline. This compound is also tested in laser-induced hypertensive monkeys, the IOP decreases from baseline.

Compound 51a is tested in normotensive dogs. The intraocular pressure (IOP) decreases from baseline. This compound is also tested in laser-induced hypertensive monkeys, the IOP decreases from baseline.

Compound 51b is tested in normotensive dogs. The intraocular pressure (IOP) decreases from baseline. This compound is also tested in laser-induced hypertensive monkeys, the IOP decreases from baseline.

Compound 58a is tested in normotensive dogs. The intraocular pressure (IOP) decreases from baseline. This compound is also tested in laser-induced hypertensive monkeys, the IOP decreases from baseline.

Compound 58b is tested in normotensive dogs. The intraocular pressure (IOP) decreases from baseline. This compound is also tested in laser-induced hypertensive monkeys, the IOP decreases from baseline.

Compound 68a is tested in normotensive dogs. The intraocular pressure (IOP) decreases from baseline. This compound is also tested in laser-induced hypertensive monkeys, the IOP decreases from baseline.

Compound 68b is tested in normotensive dogs. The intraocular pressure (IOP) decreases from baseline. This compound is also tested in laser-induced hypertensive monkeys, the IOP decreases from baseline.

Compound 70a is tested in normotensive dogs. The intraocular pressure (IOP) decreases from baseline. This compound is also tested in laser-induced hypertensive monkeys, the IOP decreases from baseline.

Compound 70b is tested in normotensive dogs. The intraocular pressure (IOP) decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula

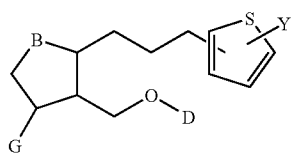

or a pharmaceutically acceptable salt thereof;

Y is

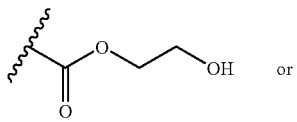

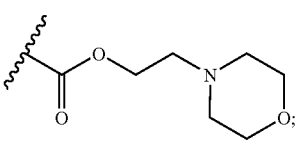

B is C=O, CH$_2$, CHOH, CHCl, CHF, CHBr, or CHCN;

G is OH or H; and

D is substituted phenyl.

2. The compound of claim 1 wherein A is 5-(3-propyl) thiophen-2-yl.

3. The compound of claim 1 wherein A is 6-hexyl.

4. The compound of claim 1 wherein A is (Z)-6-hex-4-enyl.

5. The compound of claim 1 wherein D is a dichloro substituted phenyl.

6. The compound of claim 1 wherein G is a hydroxyl.

7. The compound of claim 1 having the formula

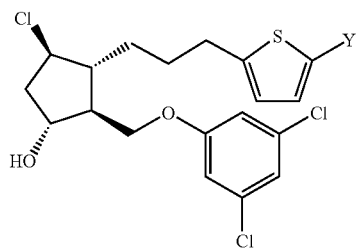

or pharmaceutically acceptable salt thereof.

8. The compound of claim 1 having the formula
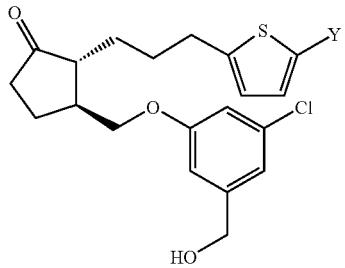
or pharmaceutically acceptable salt thereof.
9. The compound of claim 1 having the formula
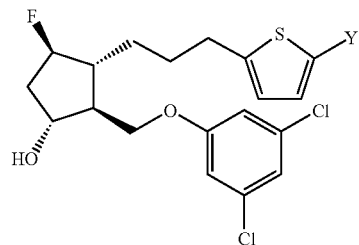
or pharmaceutically acceptable salt thereof.
10. A method for treating baldness comprising administering to a subject in need thereof a therapeutically effective amount of a compound of claim 1.
* * * * *